United States Patent
Drouaud et al.

(10) Patent No.: US 6,861,576 B1
(45) Date of Patent: Mar. 1, 2005

(54) MICROSPORE-SPECIFIC PROMOTER AND METHOD FOR OBTAINING HYBRID PLANTS

(75) Inventors: Jan Drouaud, Versailles (FR); Agnès Fourgoux, Le Fleury (FR); Georges Pelletier, Bures sur Yvette (FR); Philippe Guerche, Vanves (FR)

(73) Assignee: Institute National de la Recherche Agronomique, Paris (FR)

( * ) Notice: Subject to any disclaimer, the term of this patent is extended or adjusted under 35 U.S.C. 154(b) by 0 days.

(21) Appl. No.: 09/509,188

(22) PCT Filed: Sep. 23, 1998

(86) PCT No.: PCT/FR98/02042

§ 371 (c)(1),
(2), (4) Date: Jun. 5, 2000

(87) PCT Pub. No.: WO99/15678

PCT Pub. Date: Jan. 4, 1999

(30) Foreign Application Priority Data

Sep. 23, 1997 (FR) .......................................... 97 11812

(51) Int. Cl.[7] .......................... C12N 15/82; C12N 5/04; C12N 15/63; A01H 5/00
(52) U.S. Cl. ....................... 800/298; 800/278; 800/290; 800/287; 800/306; 536/24.1; 435/468; 435/419
(58) Field of Search ............................... 536/24.1, 23.1, 536/23.6; 800/278, 290, 287, 306, 271, 274, 303, 298; 435/468, 419, 219

(56) References Cited

U.S. PATENT DOCUMENTS

| | | | | |
|---|---|---|---|---|
| 5,689,041 A | * | 11/1997 | Mariani et al. | 800/205 |
| 5,689,049 A | * | 11/1997 | Cigan et al. | 800/287 |
| 5,993,827 A | * | 11/1999 | Sim et al. | 424/268.1 |
| 6,399,759 B1 | * | 6/2002 | Travis et al. | 536/23.2 |

FOREIGN PATENT DOCUMENTS

| | | |
|---|---|---|
| EP | 0 329 308 | 8/1989 |
| EP | 0 436 467 A2 | 7/1991 |
| EP | 790 311 A1 | 8/1997 |
| WO | 90/08828 | 8/1990 |
| WO | 90/08830 | 8/1990 |
| WO | 92/18625 | 10/1992 |
| WO | 94/13809 | 6/1994 |
| WO | 94/21804 | 9/1994 |
| WO | 94/25613 | 11/1994 |
| WO | 96/16182 | 5/1996 |

OTHER PUBLICATIONS

Izawa et al (1993, J. Mol. Biol. 230 :1131–1144).*
Hao, et al (1998, The J. of Biological Chemistry 273 (41): 26857–26861).*
Busch et al (1999, Science 285:585–587).*
Lohmann et al (2001, Cell 105 :793–803).*
Fourgoux–Nicol et al (1999, Plant Molecular Biology 40 : 857–872).*
Taylor et al (1997, The Plant Journal 12(6):1261–1271).*
Jorda et al (2000, Plant Physiology 122 :67–73).*
Segarra et al (2003, Journal of Experimental Botany 54(386):1335–1341).*
Baker et al (1992, Pesticide Science 34(2):167–182).*
Zou et al (1997, The Plant Cell 9:909–923).*
Jorda' et al., Characterization of P69E and P69F, Two Differentially Regulated Gene Encoding New Members of the . . . . , Jan. 2000, Plant Physiology, vol. 122, pp. 67–73.*
Taylor et al., Matuaration and secretion of a serine proteinase is associated with events of late microporogenesis, 1997, The Plant Journal, vol. 12, No. 6, pp. 1261–1271.*
Izawa et al., Plant bZIP Protein DNA Binding Specificity, 1993, J.Mol.Biol, vol. 230, pp. 1131–1144.*
Lohmann et al., A Molecular Link between Stem Cell Regulation and Floral Patterning in Arabidopsis, Jun. 15, 2001, Cell, vol. 105, pp. 793–803.*
Busch et al., Activation of Floral Homeotic Gene in Arabidopsis, Jul. 23, 1999, Science, vol. 285, pp. 585–587.*
Hao et al., Unique Mode of GCC Box Recognition by the DNA–binding Domain of Ethylene–responsive Elements– binding . . . , 1998, The Journal of Biological Chemistry, vol. 273, No. 41, pp. 26857–26861.*
Ballinger et al., Furilism: A Variant of Subtilism BPN' Engineered for Cleaving Tribasic Substrates, 1996, Biochemistry, vol. 35, pp. 13579–13585.*
Ramjee et al., A novel yeast expression/secretion system for the recombiant plant thiol endoprotease propapain, 1996, Protein Engineering, vol. 9, No. 11, pp. 1055–1061.*
G. Suzuki et al., "*Brassica rapa* DNA for S–locus glycoprotein, complete cds.", Jul. 10, 1997, EMBL Sequence Database Accession No. D88192, XP002068717.
G. Suzuki et al., "*Brassica rapa* DNA for S–receptor kinase, complete cds.", Jul. 10, 1997, EMBL Sequence Database Accession No. D88193, XP002068718.
M.K. Kandasamy et al., "Ablation of papillar cell function in Brassica flowers results in the loss of stigma receptivity to pollination", The Plant Cell, vol. 5, 1993, pp. 263–275, XP002067958.
M. Denis et al., "Expression of engineered nuclear male sterility in *Brassica napus* .", Plant Physiology, vol. 101, 1993, pp. 1295–1304, XP002009916.

* cited by examiner

Primary Examiner—Amy J. Nelson
Assistant Examiner—Stuart F. Baum
(74) Attorney, Agent, or Firm—Foley & Lardner LLP

(57) ABSTRACT

The invention concerns a microspore-specific promoter and its use for obtaining plants with gametophytic male sterility with inducible fertility. It also concerns a method for obtaining hybrid plants.

12 Claims, 10 Drawing Sheets

FIGURE 1

FIGURE 2

Figure 4:
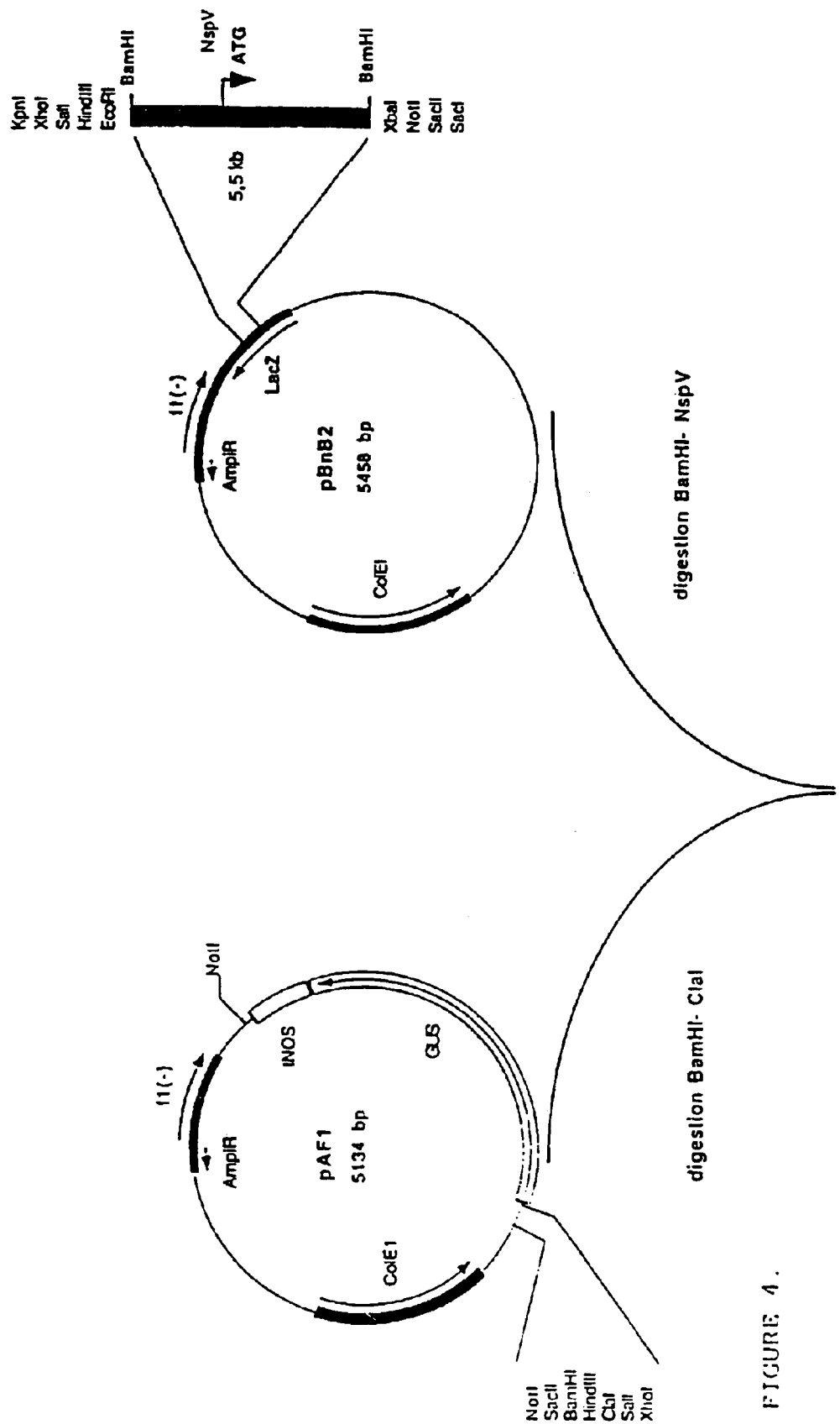
Figure 4:
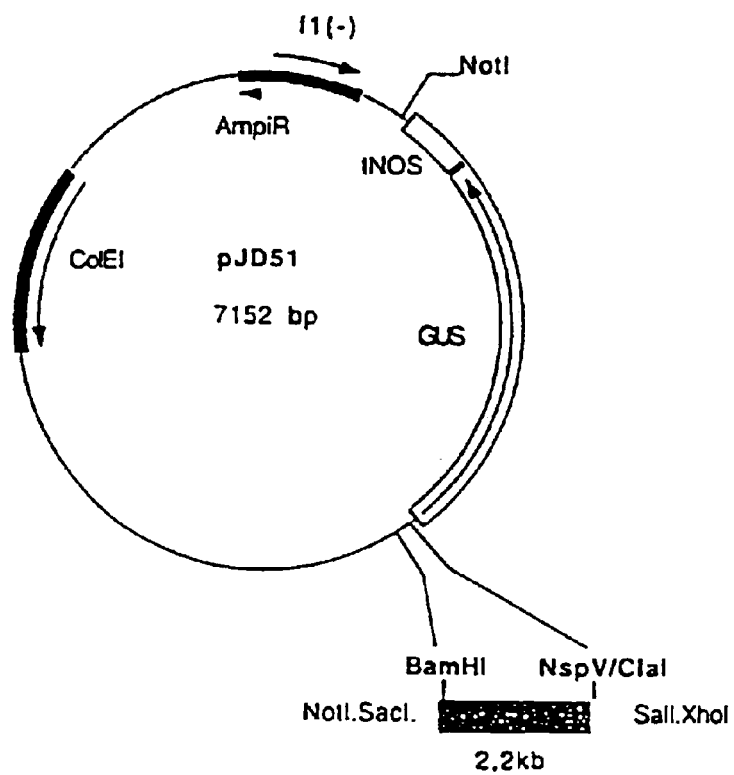

```
   1 GGATCCCACA AAGAAAACCG AAGAAGCAAA TGTTTCCTAC CTTCATAAAT
  51 ATATATTTGT TTCAGCCTCA TCAATGTACA AACAATCCTT TAGCTCAATG
 101 GTATAAATGT TGTTGTTTAG ATTTCAATAA CCCGGGTTCG AGTCATAGAC
 151 TTGACACTTT TTCACACTTT TTAAAAGTGG AACGCACATA TCGCTGACGT
 201 GTCGCATCAG GAGTGATGCA ACTGCTCTAT TATAATGTAG ATTTAAAAGT
 251 GGAACCCACG TATCGCTGAC GTGTCGCATC AGGAGTGATG CAACTGCCAT
 301 ATTATAACGT AGATTTGACG TTATTCCTTT TTAAATCTTA ATAATAATAC
 351 CAGNGCTTTT ACTTATTAAT TTTGNGCATN GTTATCATGG TTTATGCNCT
 401 CTTTTTTTTT GANCCGTTGA TTGGTTTATG CTTATTTGAA TGTNGCCNAC
 451 GTAAGAAATG AAGAACAATT TATATTTGGA GAAAATATAA TTTAATATGT
 501 TCAATATATA GAGAAAATAT TATNCCTTGA TGTTACTGTA TGGATGCGAG
 551 TAGAAGATCT TTGAATAATA TTTGAGAACT TGCCTTTTCT CAAAAAGTAA
 601 AATATTTGAT ATGTAACTTA AGTTAACACA TGAAAATTAA AAAAAAATTA
 651 AATCAAAATA GAAAAAACTG ATAGTGATCT ACCCTTCAAC GTTTTGAACT
 701 TATTCTTGGT TCACCCCCTA AACCTCTAAG TTCACCAAAC AATAAAATTT
 751 CATTATTGCA TATTCTATAT CTTTTAGAAA GTGAAACAAA ATATTATCAA
 801 GTTATATTAT GTTTTTCAAA TAAAAAGATA AAAAATAAAT AAAAAATAAT
 851 AGTAGTTACA AAAAAAAAAA ATTAATATTT TTACCAGCGT CANAAAACAC
 901 TAAAACCTAA ACCCTAAATA TTAAACTTTT AGGTAAACCC TAAACCTTTG
 951 GATAAATCTT AAACATTAAA CATTAAAACA CTAAACCCTA AATCCTAAAC
1001 TCTAAACCCT TAAGTGTTTA AATGTTTAGT GTTTTGATT TATAGTTTAG
1051 GATTTATCCA AAGGTTTAAG CTTTACCCAA GAGTTTATGG TTTAGGGATT
1101 ATGACTTAGG ATTTAGTGTT TTACTGACGA CGTTCAAAGT ATTTTTAAA
1151 AAATATTTTT TTTGTAACAA CTACTATTTT TATTTATTT TTTACCTTTT
1201 TATATTAAAA ACATAATATA ATTTAATACT CCATCTGTTT CATATTAAGT
1251 GTCATTGTAA CATTATTTTT TTGTTACAAA AAAATTGTCA CTTTAGAATT
```

FIGURE 2 (continued)

```
1301  CCAATGCAAA ATTTATTTAT TTTTCAGCTA AAATTAATTG CAAAGTGCAT
1351  TGATCTTATA AATAATTTTA TTTATCTCAA ATGCTATATT GGTCAAACAT
1401  GTGTAATTAA TAGAAACTTA ATTATATTTC ATTTATTTTT TCTTAATCTG
1451  TGTAAAAATG TCAAAGTAAA ATTTATTTAG AAACGAATTG AGTAATATTT
1501  TGTTTCATTT TTTAAAAGAT ATCGAATATG AAATAACACA ATTTTATTGT
1551  ATGATGAACC TAAAAATTCA TCCTAAGAAG GTGAACGCAA GAATAAGTCA
1601  ACGTTTTGGG GAAAGCTAAC TATGGCCCAA AGTCATCAAA ATCTTTCTTG
1651  TATTTATCAA AATCCTTACA AATTTAGTTA GAGTTAATAG ACCAAACACA
1701  TGATTATCAT CATATTAGAA TATTCTAAAA AATTACTAGC GAATAATTAA
1751  AATCTTTCTT TTATTTATCA AAATCCTTAT AAAAACTTAT TTATATATAC
1801  TAAAACAATT TTAATTAAAA GAAAATAAGG GACCATGGAT ACATAAAAAT
1851  ATATGTTATT TCTTAAGATA GTGATAATAT TAATATATAC CAGTCCATAT
1901  ATTTATCAAA ATAAATAATA TTTTTCGTAG TCCGATAATC ATTACTATAA
1951  ATTCATAAAA CCACATGTAG ATGTATATTT TATTTATATA TATATATATA
2001  AACCCTAACG CCTTACCACT CGATAACCAT CAAAACTTTT CTTCTCGTTT
2051  CGCTAACTCA AGGCTTCGAA AAGTAAAAAA AACAATGAAG AATGTCACAC
2101  TTGTTCTTGC TATGATCCTC TTCTTAAGCT GTGTCACATC CAAAGTTACA
2151  GCAACAGAAC TAGAGTCATC AACTAACCAA GAGCTCTTCC TATCGCGGCA
2201  CTTACCTCGC TTTCACCCCA AGCAACATTG GCCGTTCCGT GGCTCCGGAA
2251  AAGCCTTCCC TGCAGGCCAC TTCCGACTAA CTCCGTTCCA TCTGCCACAG
2301  GAAGTCACCA GATGCTTGAA CGACAAGAAG GAGGTAGGTA CATGTTTTAA
2351  TGATATCGCT GAGACTTTCT TCACCAGGAA AGCCGCTATT GGATCGGAAT
2401  GTTGCGCCGC GATCAAGAAG ATGAACAAAG ATTGTGAGAA GACCGTCTTT
M3                                                       TTT
2451  GGATCTTTCC ATGACCCCTT CTTGACCGGC TATGTCAAGC TACATTGCTC
M3    GGATCTTTCC ATGACCCCTT CTTGACCGGC TATGTCAAGC TACATTGCTC
2501  CACCGTTGTT GGATCTACTT CACCTCCTCC TTCACAGGCT CCTTTACATG
M3    CACCGTTGTT GGATCTACTT CACCTCCTCC TTCACAGGCT CCTTTACATG
```

```
2551  CTCCTTCTTC ACAGGCTCCT TCACATGCTC CTTCACATGC TCCTTCACAG
  M3  CTCCTTCTTC ACAGGCTCCT TCACATGCTC CTTCACATGC TCCTTCACAG

2601  GCTCCTTTAA ATGCTCCTTT AAATGCTCCT TTACATGCTC CTTTACATGC
  M3  GCTCCTTTAA ATGCTCTTTT AAATGCTCCT TTACATGCTC CTTTACATGC

2651  TCCTTCACAG GCCCCTTCAC AGGCCCCTTC ACAGGCCCCT TTACATGCTC
  M3  TCCTTCACAG GCCCCTTCAC AGGCCCCTTC ACAGGCCCCT TTACATGCTC

2701  CTTTACTGCC CCCTTCGCAG GCTCCTTCAC CGGCTCAGTG ATTTAGCTAT
  M3  CTTTACTGCC CCCTTCGCAG GCTCCTTCAC CGGCTCAGTG ATTTAGCTAT

2751  TTGATAGAAT TATTCAAGTA TTGATGTCCT AGGGAGTTTT AGTTTTTTTC
  M3  TTGATAGAAT TACTCAAGTA ATGATGCCCT AGGGAGTTTG AGTTTTTCTC

2801  TTGTTTTAAA ATTTTGTGTT TATTTTGAGA AAACCGTCTT TGGATTTTAA
  M3  GTGTTTTAAA GTTTTGTGTT TATTTTGAGA AAACCGTCTT TGGATTTTAA

2851  CTT
  M3  CTT
```

MICROSPORE-SPECIFIC PROMOTER AND METHOD FOR OBTAINING HYBRID PLANTS

This application is filed under 35 U.S.C. § 371 from PCT/FR98/02042, filed Sep. 23, 1998.

The present invention concerns in particular a microspore-specific promoter and a method for producing hybrid plants.

The microspore corresponds to a precise stage in the development of the male gamete in higher plants. Male gametogenesis takes place in a specialized organ, the anther, and comprises sensu stricto the differentiation of diploid cells into haploid pollen grains. Each diploid cell, called a sporogenic cell, undergoes meiosis to produce four haploid microspores which subsequently differentiate to give mature pollen grains.

Knowing the molecular factors which control the development of the microspore, and how to manipulate them, is a considerable asset not only from a fundamental research point of view but also from a plant-improvement point of view. This is because this knowledge enables the production of pollen grains, and consequently the reproduction of the plant, to be controlled.

Such control proceeds via the production of plants with one of their gametes totally sterile so as to prevent self fertilization.

So far, male sterility of plants, which is less complex than female sterility, has been widely studied but necessitates the use of genetic systems which are relatively laborious to implement for commercial production of hybrid seeds. One type of male sterility which is highly used is cytoplasmic male sterility which consists in producing:

- a female line whose sterile-male characteristic is transmitted through the cytoplasm; such a cytoplasm is called a "male-sterility-inducing cytoplasm"; these "inducing cytoplasms" are, for a given species, in general discovered in the wild, or sometimes observed in plants which result from interspecific crosses (cross-fertilization, protoplast fusion, etc.),
- a "sterility-maintaining" line whose cytoplasm is normal, and
- a fertility-restoring line if the seeds and/or the fruit of the hybrid plant are harvested.

In the female line (carrier of the sterility-inducing cytoplasm) all the pollen grains are killed. To multiply and improve this line it is therefore necessary to have a line which carries neither the (inducing cytoplasm (which thus produces pollen grains) nor the restoration gene. This line is termed "sterility-maintaining" because crossing with the female line gives an entirely female lineage.

Restoration of the fertility is carried out in the hybrid by crossing the female parent (carrying the sterile male cytoplasm) with the parent comprising a nuclear restoration gene (the restoring line), this cross enabling the production of fertile hybrid plants which will produce seeds by self-fertilization.

In the case of sporophytic nuclear sterility, systems have been described, for example, which make it possible to kill the mother cells of the microspores by means of an RNAse, and, consequently, to, obtain plants lacking in the male gametes. The fertility is restored when the line which no longer produces male gametes is crossed with another line carrying an inhibitor of the RNAse, the seeds resulting from this cross comprising both the cytotoxic gene and its inhibitor.

As for the present invention, it proposes to produce plants with gametophytic male sterility, which are incapable of producing pollen grains. It consists in using a promoter region which controls the expression, specifically in the microspores, of a gene encoding a cytotoxic molecule, while also having a means permitting the controlled inhibition of this toxicity, in order to obtain a line of homozygous progenitor plants which are totally sterile as regards their male gametes, and then to obtain fertile hybrid plants (which produce one viable pollen grain in two), thus capable of producing seeds, without having to resort to using a fertility restoration gene.

So far, a single gene which is expressed specifically in the microspore has been described, in tobacco (Oldenhof et al., 1996). This gene does not have any homology with the Brassicaceae as results from a Southern Blot experiment on the genomic DNA of Brassica oleracea (data not shown).

A subject of the present invention is therefore a nucleotide sequence for which it has been demonstrated that the corresponding gene is expressed specifically in the microspore; this nucleotide sequence corresponds to SEQ ID No. 3.

Consequently, a subject of the present invention is a nucleotide sequence corresponding to all or part:

a) of the sequence according to SEQ ID No. 3, or b) of a sequence which hybridizes to the sequence according to a), or c) of a sequence which has at least 80% homology with a) or b).

In the context of the present invention, the most valuable part of this nucleotide sequence is the promoter region which is defined as being the sequence preceding (on the 5' side) the translation start codon (ATG). However, at the current stage of knowledge about the nucleotide sequence according to SEQ ID No. 3, three ATGs have been shown: one at position 1965, another at position 2085 and a third at position 2112. It would appear that the functional ATG is the one situated at position 2085. This is not confirmed however; it is the reason why the largest envisagable promoter region concerning SEQ ID No. 3 stretches from nucleotide 1 to nucleotide 2111, and preferably from nucleotide 1 to nucleotide 2084.

This promoter region thus precedes, in the natural state, a coding (orf) sequence which is expressed specifically in the microspores, and in the case where this orf is replaced (by genetic manipulation) by another orf whose product is a cytotoxic molecule, the latter is capable of destroying only said microspores.

A subject of the invention is therefore also cellular expression vectors, comprising a promoter sequence such as that described above, placed upstream of a DNA sequence encoding a cytotoxic product.

Advantageously, the cytotoxic product in question is a protease. Specifically, when the protease is expressed specifically in the microspores, it destroys all the proteins thereof, as a result of which the microspore cannot survive. Preferably, the protease is a subtilisin, and in particular the BPN' subtilisin from Bacillus amyloliquefasciens. This BPN' subtilisin is part of the family of subtilisins which are found in many organisms and which are proteases known to cleave proteins at the level of serines.

It involves, therefore, introducing a vector in accordance with the invention into a bacterial strain capable of carrying out the transformation of plant cells, such as Agrobacterium tumefaciens. This may in particular be carried out by the method of infiltration of Arabidopsis thaliana plants described by Bechtold et al., 1993. This technique consists in introducing the bacterium into the cells of the floral scapes by infiltration under vacuum. The plants are then bedded out under glass and their seeds harvested. About one seed in a thousand gives rise to plants of which all the cells carry the transgene. The transformation of other plants, and in particular of rape, may be carried out through *Agrobacterium tumefaciens* and/or *Agrobacterium rhizogenes* with the aid of various techniques, now conventional (transformation of foliar disks, of hypocotyls, of floral scapes etc.) which combine a phase of coculture of the bacterium with the plant tissues, followed by the selection and by the regeneration of the transformed cells into whole plants. Other transformation techniques do not use this bacterium, but make it possible to transfer the cloned gene directly into cells or tissues (electroporation, particle gun etc.), and to select and obtain transformed plants (review by Siemens and Schieder).

A subject of the present invention is also the cells of plants transformed with a vector in accordance with the invention and plants comprising said cells.

A subject of the invention is also plants with gametophytic male sterility with inducible fertility, comprising a gene encoding a male-gamete-specific cytotoxic product.

As indicated above, the present invention thus enables the production of plants with gametophytic male sterility which inhibits any production of pollen grains. However, these plants, which are homozygous as regards their male sterility, may be obtained only after self-fertilization of plants which have previously been transformed with a vector in accordance with the invention, i.e. which are hemizygous as regards their male sterility and in which the fertility of the pollen grains carrying the gametophytic sterility has been provisionally restored, so as to allow them to carry out self-fertilization.

One means of producing plants which are homozygous for this gene would be to use gynogenesis, a technique which consists in regenerating doubled haploid plants from ovule or ovary culture. It involves, in this case, obtaining the formation of a homozygous diploid plant from a female haploid gamete. Gynogenesis, is applicable to a certain number of plant species, but production of a large number of plants which are homozygous for the transgene in question is not envisagable by this technique, because it is tricky to use and its efficacy most often remains very poor.

The present invention also concerns a method for producing plants with gametophytic male sterility with inducible fertility, comprising:

the insertion into plants of line A of a gene whose expression product is cytotoxic for the microspores, and the production of plants which do not produce male gametes.

More particularly, the method for producing plants with gametophytic male sterility with inducible fertility in accordance with the invention comprises the steps of:

a) transformation of plants of a line A with a vector in accordance with the invention, b) induction of the fertility of the plants obtained in a) by inhibition of the cytotoxicity of the product, c) self-fertilization of the fertile plants obtained in b), d) selection of the plants which do not produce male gametes, derived from c), e) multiplication of the plants obtained in d) by repeating steps b) and c).

Thus, in step a) of the method above, a line A is transformed with a vector in accordance with the invention, i.e. comprising a microspore-specific promoter sequence placed upstream of a gene encoding a cytotoxic product. The plants resulting from this transformation all comprise the DNA in question whose gene is expressed only in the microspores. However, at this stage, the plant being diploid at the time of the transformation, it becomes heterozygous as regards its male sterility and is therefore capable, after transformation, of giving rise to microspores of which only 50% are viable (the other 50% being destroyed following the expression of the transformant).

In step b), the restoration or the induction of the fertility which has been lost by the transformed plant is then carried out by inhibiting the toxicity of the product of the transforming gene.

This may be done in various ways. However, when the cytotoxic product in question is a subtilisin and in particular the BPN' subtilisin from *Bacillus amyloliquefasciens*, the inhibition is achieved by the action on the transformed plant of an insecticide molecule of the fluorophosphate family (having a priori no action on the plants). Indeed, this molecule, applied during anthesis, is capable of restoring the total fertility of the hemizygous plants by inhibition of the subtilisin. It may, for example, be applied to the foot of the plant and reach all the tissues. As an insecticide, it should have no effect on the plant. However, it will have its full effect at the level of the microspores, the only organs which express subtilisin.

Next, in step c), the self-fertilization of the plants whose fertility has been restored is carried out, then, in step d), the plants which are homozygous with respect to male sterility, and consequently totally sterile in th absence of treatment i.e. of inhibition of the cytotoxic product, are selected.

The plants thus obtained, which are incapable of producing male gametes but still capable of producing female gametes, i.e. ovules, may be crossed with another line of plants which are totally fertile and have valuable agronomic properties. In this cross, the plant which is homozygous as regards male sterility plays the role of the female parent whilst the other plant plays the role of the male parent. The hybrid resulting from this cross is hemizygous as regards male sterility, and is therefore capable of producing pollen grains of which 50% are viable (the others, carrying the transgene, are thus destroyed by the cytotoxic product). A 50% production of the pollen is more than enough to give rise to seeds having the qualities of each of the crossed lines which it is specifically desired to combine.

The present invention thus also concerns a method for producing hybrid plants, characterized in that it comprises crossing plants of line A, which have gametophytic male sterility as described above, with plants of line B of agronomic value. It also concerns the seeds derived from the hybrid plants thus obtained.

Advantageously, the plants in accordance with the invention belong to the *Brassicacea* family; preferably, they are rape.

In addition, it should be pointed out that the promoter region in accordance with the invention may also be used in strategies of gene inactivation by utilization of mobile elements such as transposons and retrotransposons.

Specifically, this may be carried out with the aim of isolating plants which have a stable mutant genotype, and isolating a very large number of different, independent mutants.

It involves creating a chimeric sequence consisting of a promoter region in accordance with the invention and of the sequence, all or in part, of a mobile element. The expression of this mobile element, which is reduced to the phase of development of the microspore, should make it possible to induce some mutations into the genome of the pollen grains of the transformed plant. It is thus possible, in the lineage obtained from these pollen grains, to isolate individuals which no longer carry the transgene, but merely one or more mutations derived from transposition phenomena. The principle is to bring about, using the abovementioned promoter region, activation of the transposition of these mobile elements for a very short time (microsporogenesis) in a multitude of gametic cells and to eliminate in the following generation the plants which carry the transgene (i.e. the promoter region+the sequence which allows the activation of the transposition) so that the cycle does not start up again. It then involves investigating, in the lineage, and by various techniques, the plants for which the mobile elements have caused mutations by inserting themselves into genes. The study of these plants would make it possible, in particular, to understand the function of the mutated gene.

Among the mobile elements which can be used in this way, mention may be made of the retrotransposons of the type Tnt1, Tto1, Tnp-2, Tos10-17, Bs1, BARE-1, Ta-1, etc., or the transposons of the type Ac/Ds, Spm, Mu, etc.

Figure 1:
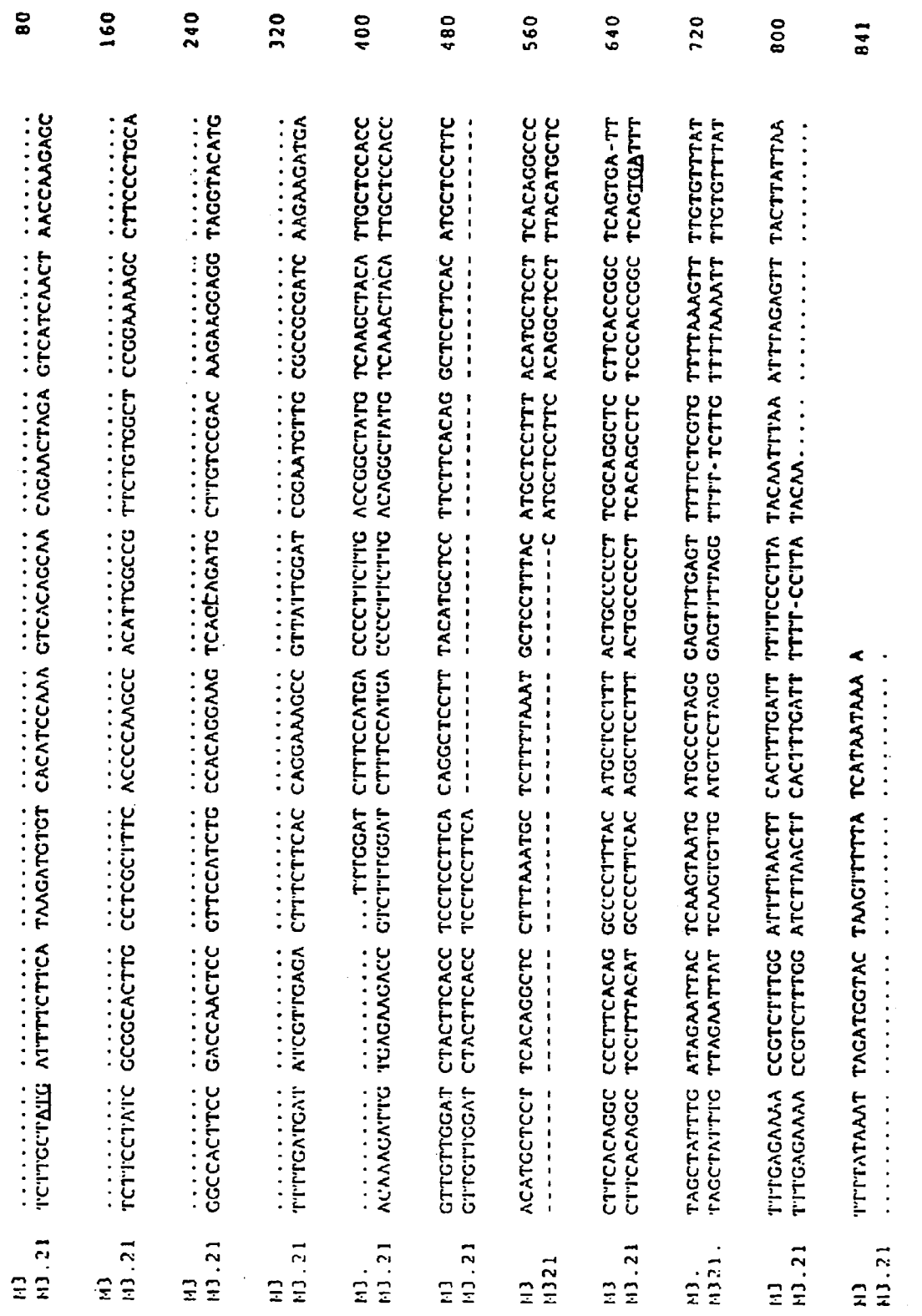

FIG. 1 illustrates the alignment of the sequences of the two cDNAs M3 (SEQ ID No. 1) and M3.21 (SEQ ID No. 2) derived from the screenings of the *Brassica napus* cv.Brutor microspore cDNA library. The start (ATG) and stop (TGA) codons of the putative coding sequence are underlined.

FIG. 2 gives the nucleotide sequence of the clone BnM3.4 (SEQ ID No. 3) from which the M3 cDNA is thought to be derived. The ATG in bold (position 2085) the one which has the highest probability of being the functional ATG. The ATG underlined in position 2112 is the one present in the M3.21 cDNA sequence. The ATG underlined in position 1965 is the first ATG encountered. The sequence preceding these ATGs is, consequently, taken to be the promoter region of the BnM3.4 gene.

Figure 3:
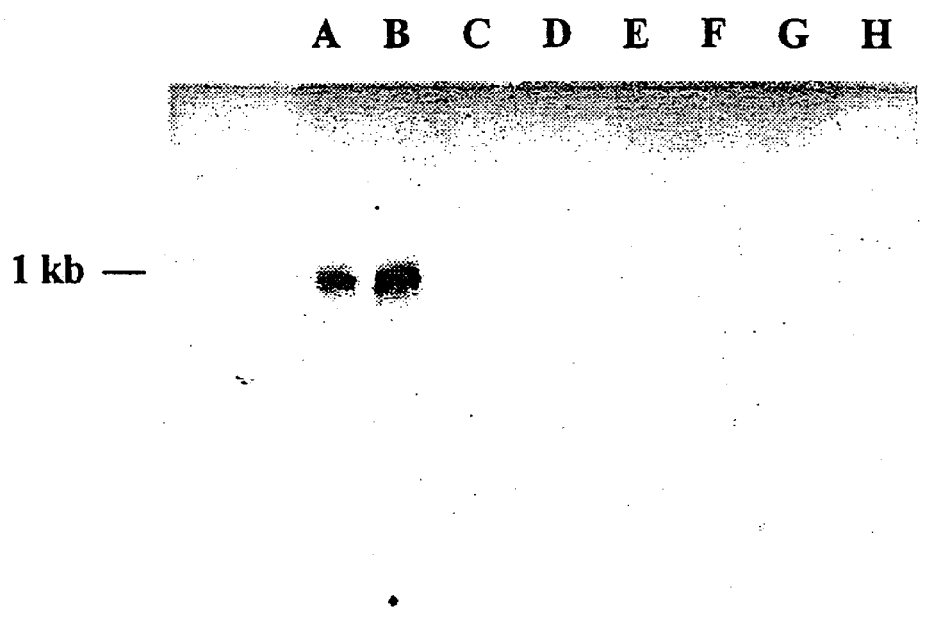

FIG. 3 illustrates the Northern Blot hybridization with the $P^{32}$-labeled M3 probe on total RNAs (10 µg per well) extracted from different rape tissues. A: buds of 0–2 mm (meiocytes); B: buds of 2–3 mm (mononucleated microspores); C: buds of 3–4 mm (binucleated microspores); D: buds greater than 4 mm (mature pollen grains); E: rape sepals; F: rape pistils; a: buds of sterile male rape; H: full buds of rape.

FIG. 4 illustrates the preparation of the 7152 bp pJD51 plasmid from the 5135 bp pAF1 plasmid (plasmid of origin: pBluescript SK-PROMEGA) and from the 5458 bp pBnB2 plasmid (plasmid of origin pBS SK-PROMEGA).

Figure 5:
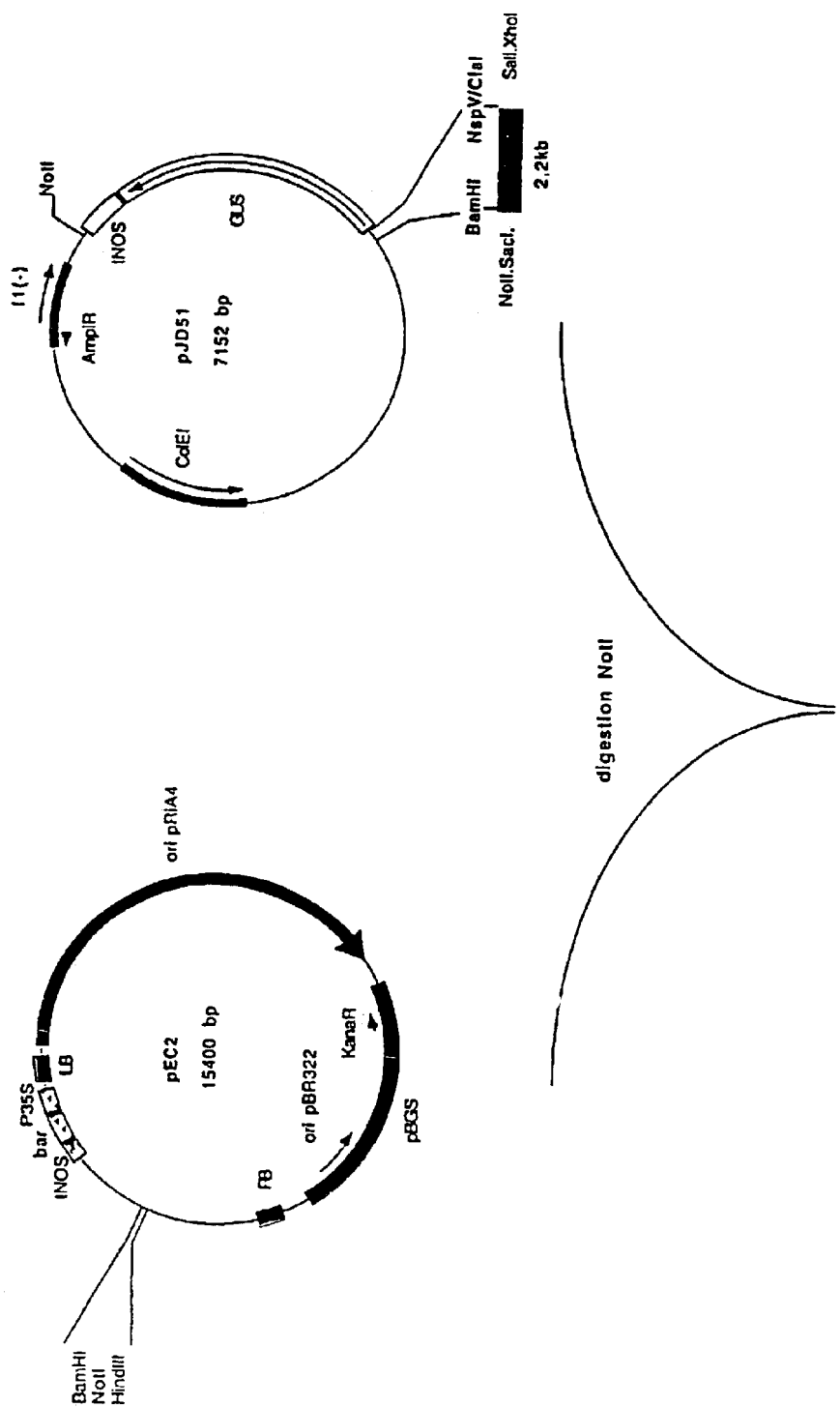
Figure 5:
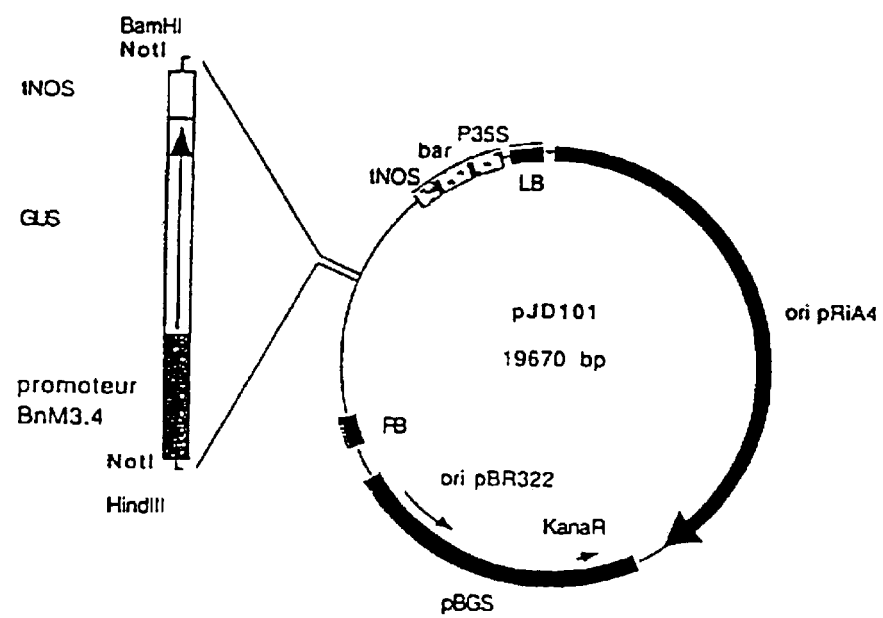

FIG. 5 illustrates the preparation of the 19670 bp pJD101 plasmid from the 15400 bp pEC2 plasmid which is derived from the PDHB 321.1 plasmid (D. Bouchez, personal communication) and from the pJD51 plasmid (cf. FIG. 2).

Figure 6:
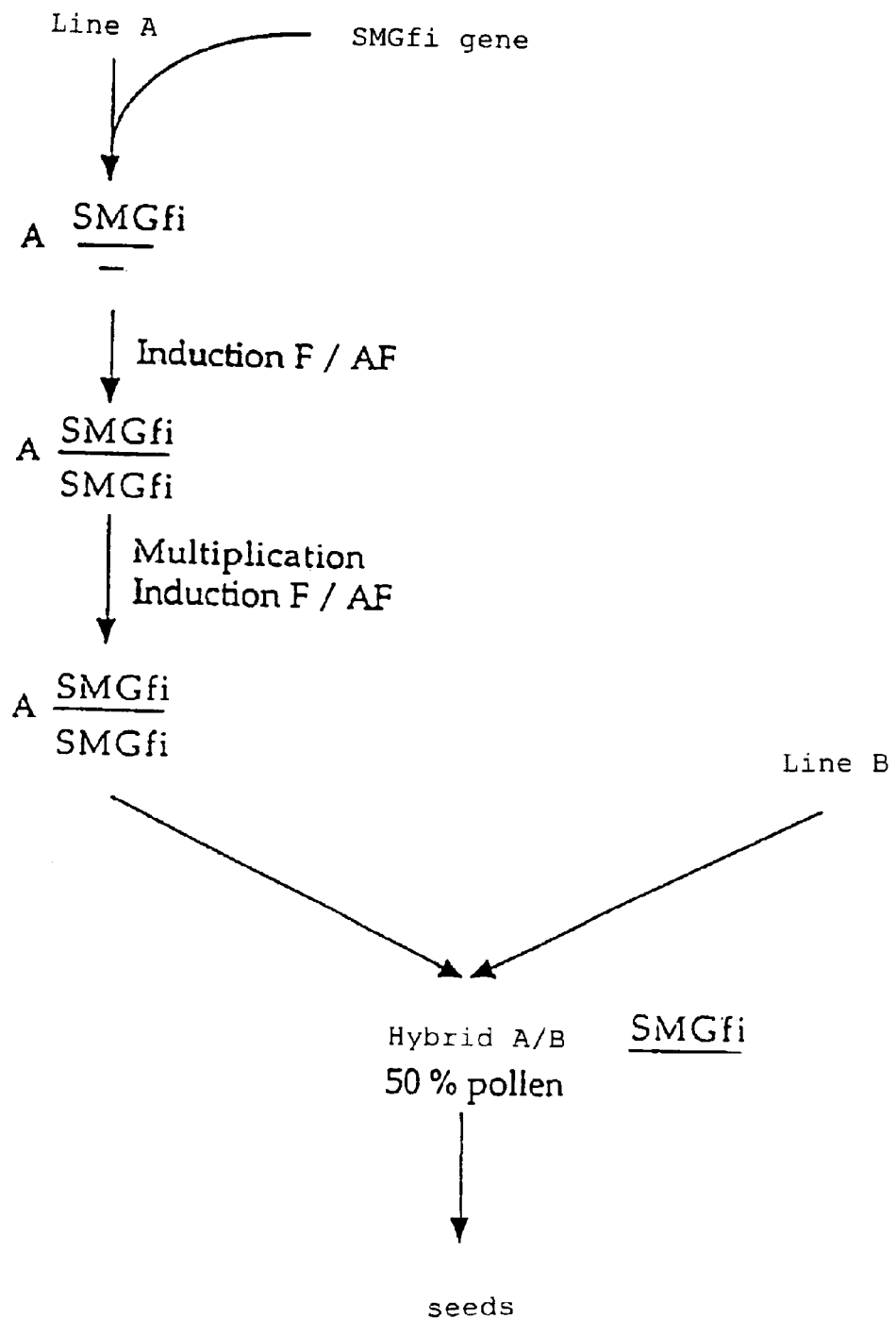

FIG. 6 represents a scheme of selection of hybrid varieties of a plant (rape for example) which calls upon a system of gametophytic male sterility with induction of the fertility. SMGfi: gametophytic male sterility with inducible fertility; Induction F: induction of the fertility; AF: self-fertilization.

The invention is not limited to the sole description above; it will be better understood in the light of the following examples, which are given, however, purely as illustrations.

EXAMPLE 1

Demonstration of a Microspore-Specific Promoter

The first step consisted in producing complementary DNA (cDNA) clones expressed specifically in the microspore of rape. For this, cDNAs were synthesized from rape microspore messenger RNAs (mRNA). In parallel, cDNAs were synthesized from floral bud mRNA from sterile male rape. The cDNAs coming from said floral buds were subtracted from the cDNAs derived from the mRNAs expressed in the microspore of rape. The molecules resulting from this subtraction were used in an experiment of differential hybridization of a microspore cDNA library, according to a technique similar to that presented by Atanassov et al. (1996).

One of these isolated clones, the M3 cDNA (SEQ ID No. 1), proved to be the representative of an mRNA which is specifically expressed in the microspore of rape. Another cDNA, named M3.21 (SEQ ID No. 2) was found by screening the library with the M3 cDNA. The sequences of these two cDNAs show 89% identity (FIG. 1); they are clearly derived from a family of very close genes, which are expressed specifically in the microspore.

The M3 cDNA clone was used as a probe to screen a rape genomic DNA library sold by CLONTECH Laboratories, Inc., 4030 Fabian Way, Palo Alto, Calif. 94303-4607, USA; two clones (BnM3.4 and BnM3.2) corresponding to two different genes were isolated. The M3 cDNA is thought to be derived from the BnM3.4 (SEQ ID No. 3) gene, because this gene carries an orf which is identical to the M3 cDNA (FIG. 2). This gene has no intron. Sufficient experimental results lead to the thought that the M3.21 cDNA is not derived from the second isolated gene (BnM3.2), which indeed carries a region corresponding to the M3.21 cDNA sequence, but to a third gene, which is very close to the BnM3.2 gene.

The promoter region of this gene is defined as being the sequence immediately upstream of the translation start codon (ATG).

EXAMPLE 2

Verification of the Specificity of the Promoter of the BnM3.4 Gene

A/ Northern Blot

A Northern Blot analysis was carried out with 10 µg of total RNA from sepals, pistil, whole buds, buds from sterile male plants, meiocytes, microspores, binucleated pollen grains and trinucleated pollen grains, hybridized with the M3 cDNA. A band of 1 kb corresponds to the transcript of the BnM3.4 gene, and also to the M3.21 transcript, since they are very close sequences. These transcripts are present uniquely in the first two stages of male gametogenesis, whose products are difficult to isolate perfectly experimentally (FIG. 3).

The proteins deduced from these two cDNA clones are evidently very close and are rich in glycine and proline. They are identical to strictly no other protein in the databanks, but are certainly involved in the formation of the wall.

B/ Transformation with a Chimeric Gene

Different chimeric genes (i.e. consisting of the sequence encoding a known gene, preceded by the promoter region in accordance with the invention) were constructed in order to study the spatio-temporal specificity of the BnM3.4 promoter.

FIG. 4 shows the construction of a bacterial vector pJD51, which combines a fragment of the BnM3.4 promoter with the sequence encoding the β-glucuronidase gene. The pAF1 plasmid containing the sequence encoding β-glucuronidase and the transcription termination sequence of the NOS gene from *Agrobacterium tumefaciens*, was digested with the enzymes BamHI and ClaI. The pBnB2 plasmid contains a 6 kb BamHI-BamHI fragment derived from the BnM3.4 genomic DNA clone, and in which the BnM3.4 gene is present. A fragment corresponding to the largest promoter region possible given the restriction sites (2056 bp) was isolated from the pBnB2 plasmid by a BamNH-NspV digestion, and inserted between the BamHI and ClaI (compatible with NspV) sites of the pAF1 plasmid.

The chimeric gene thus constructed was isolated by a NotI digestion of the pJD51 plasmid, so as to be cloned into a binary plasmid from *Agrobacterium tumefaciens*: pEC2 opened by the enzyme NotI (FIG. 5).

The pJD101 binary plasmid containing the chimeric gene was introduced into the C58C1 strain (pMP90) of *Agrobacterium tumefasciens* (Koncz et al. 1986) by electroporation, and the transformants possessing pJD101 were selected on a medium containing kanamycin. One of these *Agrobacterium* transformants was used to transform *Arabidopsis thaliana* (Wassilevskja ecotype) by the method of infiltration of the floral scapes described by Bechtold et al., 1993. The transformed plants are selected using their resistance to phosphinothrycin, which is conferred by a resistance gene jointly inserted into the T-DNA.

Among these plants, certain show expression of the β-glucuronidase specifically in the microspores (demonstrated by a blue coloration when a β-glucuronidase-specific substrate, X-Glu, is added). No coloration is present in the adjacent tissues of the anther, nor in the somatic tissues of the plant. In a transformed plant which is, hemizygous for the chimeric gene, half the microspores produced are blue, because only they contain the chimeric gene.

The specificity of expression conferred by this 2 kb promoter sequence is indeed restricted, within the limits of the sensitivity of the technique, to a single cell type, and from the microspore stage.

REFERENCES

Atanassov I et al. (1996) Plant Science 118, 185–194
Bechtold N. et al. (1993) Comptes-Rendus de l'Académie des Sciences 316, 1194–1199
Koncz et al. 1986) Molecular General Genetics 204, 383–396
Mariani et al. Nature 347 (1990) 737–741
Oldenholf M. T. et al. (1996) Plant Molecular Biology 31, 213–225
Siemens and Schieder 1996. Plant Tissue Culture and Biotechnology, 2, 66–75

What is claimed is:

1. A purified promoter comprising: nucleotides 1–2056 of SEQ ID NO:3 wherein the promoter is capable of directing expression of a second nucleotide sequence to which it is operably linked.

2. An expression vector comprising the promoter according to claim 1, wherein said promoter is upstream of and operably linked to a DNA sequence encoding a protein that is capable of destroying a microspore.

3. The expression vector of claim 2, wherein the protein is a protease.

4. A plant cell transformed with the vector of claim 2.

5. A plant comprising the cell of claim 4.

6. A plant having gametophytic male sterility with inducible fertility, comprising a nucleotide sequence encoding a protein, which is operably linked to a male-gametophyte-specific promoter comprising nucleotides 1–2056 of SEQ ID NO:3, and wherein the protein is capable of destroying a microspore.

7. A method for producing a plant with gametophytic male sterility with inducible fertility, comprising inserting into one or more plant cells a construct that contains a nucleotide sequence that is operably linked to a gametophyte-specific promoter, wherein the expression product of said nucleotide sequence is capable of destroying a microspore; and regenerating a plant therefrom which does not produce a male gamete, wherein said gametophyte-specific promoter comprising nucleotides 1–2056 of SEQ ID NO:3, and wherein said promoter is capable of directing expression of said nucleotide sequence.

8. The plant of claim 6, wherein said plant belongs to the *Brassicaceae* family.

9. A seed from the plant of claim 6, wherein said seed comprises said male-gametophyte-specific promoter operably linked to said nucleotide sequence encoding said protein.

10. The plant of claim 8, wherein said plant is rape.

11. The plant obtained by the method of claim 7, wherein said plant belongs to the *Brassicaceae* family.

12. The plant of claim 11, wherein said plant is rape.

* * * * *

SEQUENCE LISTING

<160> NUMBER OF SEQ ID NOS: 3

<210> SEQ ID NO 1
<211> LENGTH: 497
<212> TYPE: DNA
<213> ORGANISM: Brassica napus
<220> FEATURE:
<223> OTHER INFORMATION: M3

<400> SEQUENCE: 1

```
tttggatctt tccatgaccc cttcttgacc ggctatgtca agctacattg ctccaccgtt        60
gttggatcta cttcacctcc tccttcacag gctccttac atgctccttc ttcacaggct       120
ccttcacatg ctccttcaca tgctccttca caggctcctt taaatgctct tttaaatgct       180
cctttacatg ctcctttaca tgctccttca caggcccctt cacaggcccc ttcacaggcc       240
cctttacatg ctcctttact gccccttcg caggctcctt caccggctca gtgatttagc       300
tatttgatag aattactcaa gtaatgatgc cctagggagt ttgagttttt ctcgtgtttt       360
aaagttttgt gtttattttg agaaaaccgt ctttggattt taacttcact ttgatttttt       420
cccttataca atttaaattt agagtttact tattaatttt ataaattaga tggtactaag       480
tttttatcat aataaaa                                                      497
```

<210> SEQ ID NO 2
<211> LENGTH: 674
<212> TYPE: DNA
<213> ORGANISM: Brassica napus
<220> FEATURE:
<223> OTHER INFORMATION: M3.21

<400> SEQUENCE: 2

```
tcttgctatg attttcttca taagatgtgt cacatccaaa gtcacagcaa cagaactaga        60
gtcatcaact aaccaagagc tcttcctatc gcggcacttg cctcgctttc accccaagcc       120
acattggccg ttctgtggct ccggaaaagc cttccctgca ggccacttcc gaccaactcc       180
gttccatctg ccacaggaag tcaccagatg cttgtccgac aagaaggagg taggtacatg       240
```

-continued

```
ttttgatgat atcgttgaga cttctcttcac caggaaagcc gttattggat cggaatgttg    300
cgccgcgatc aagaagatga acaaagattg tgagaagacc gtctttggat ctttccatga    360 cccttcttg acaggctatg tcaaactaca ttgctccacc gttgttggat ctacttcacc     420
tcctccttca catgctcctt cacaggctcc tttacatgct ccttcacagg ctcctttaca    480
tgccccttca caggctcctt tactgccccc ttcacagcct ctcccaccgg ctcagtgatt    540
ttagctattt gttagaatta ttcaagtgtt gatgtcctag ggagtttag gttttttcttg    600 ttttaaaatt ttgtgtttat tttgagaaaa ccgtctttgg atcttaactt cactttgatt    660
ttttccttat acaa                                                      674
```

```
<210> SEQ ID NO 3
<211> LENGTH: 2853
<212> TYPE: DNA
<213> ORGANISM: Brassica napus
<220> FEATURE:
<221> NAME/KEY: modified_base
<222> LOCATION: (354)
<223> OTHER INFORMATION: a, c, t, g, other or unknown
<221> NAME/KEY: modified_base
<222> LOCATION: (375)
<223> OTHER INFORMATION: a, c, t, g, other or unknown
<221> NAME/KEY: modified_base
<222> LOCATION: (380)
<223> OTHER INFORMATION: a, c, t, g, other or unknown
<221> NAME/KEY: modified_base
<222> LOCATION: (398)
<223> OTHER INFORMATION: a, c, t, g, other or unknown
<221> NAME/KEY: modified_base
<222> LOCATION: (413)
<223> OTHER INFORMATION: a, c, t, g, other or unknown
<221> NAME/KEY: modified_base
<222> LOCATION: (444)
<223> OTHER INFORMATION: a, c, t, g, other or unknown
<221> NAME/KEY: modified_base
<222> LOCATION: (448)
<223> OTHER INFORMATION: a, c, t, g, other or unknown
<221> NAME/KEY: modified_base
<222> LOCATION: (524)
<223> OTHER INFORMATION: a, c, t, g, other or unknown
<221> NAME/KEY: modified_base
<222> LOCATION: (893)
<223> OTHER INFORMATION: a, c, t, g, other or unknown
<223> OTHER INFORMATION: BnM3.4
```

<400> SEQUENCE: 3

```
ggatcccaca aagaaaaccg aagaagcaaa tgtttcctac cttcataaat atatatttgt    60
ttcagcctca tcaatgtaca aacaatcctt tagctcaatg gtataaatgt tgttgtttag   120
atttcaataa cccgggttcg agtcatagac ttgacacttt tcacacttt ttaaaagtgg    180 aacgcacata tcgctgacgt gtcgcatcag gagtgatgca actgctctat tataatgtag    240
atttaaaagt ggaacccacg tatcgctgac gtgtcgcatc aggagtgatg caactgccat    300
attataacgt agatttgacg ttattccttt taaatctta ataataatac cagngctttt     360
acttattaat tttgngcatn gttatcatgg tttatgcnct ctttttttt ganccgttga     420 ttggtttatg cttatttgaa tgtngccnac gtaagaaatg aagaacaatt tatatttgga    480
gaaaatataa tttaatatgt tcaatatata gagaaaatat tatnccttga tgttactgta    540
tggatgcgag tagaagatct ttgaataata tttgagaact tgccttttct caaaagtaa    600 aatatttgat atgtaactta agttaacaca tgaaaattaa aaaaaatta atcaaaata     660 gaaaaaactg atagtgatct acccttcaac gttttgaact tattcttggt tcaccccta     720 aacctctaag ttcaccaaac aataaaattt cattattgca tattctatat cttttagaaa    780
```

-continued

```
gtgaaacaaa atattatcaa gttatattat gtttttcaaa taaaaagata aaaaataaat      840
aaaaaataat agtagttaca aaaaaaaaaa attaatattt ttaccagcgt canaaaacac      900
taaaacctaa accctaaata ttaaacttttt aggtaaaccc taaacctttg gataaatctt     960
aaacattaaa cattaaaaca ctaaacccta aatcctaaac tctaaaccct taagtgttta     1020
aatgtttagt gttttttgatt tatagtttag gatttatcca aaggtttaag gtttacccaa    1080
gagtttatgg tttagggatt atgacttagg atttagtgtt ttactgacga cgttcaaagt    1140 atttttttaaa aaatattttt tttgtaacaa ctactatttt tatttatttt tttacctttt    1200
tatattaaaa acataatata atttaatact ccatctgttt catattaagt gtcattgtaa    1260
cattattttt ttgttacaaa aaaattgtca ctttagaatt ccaatgcaaa atttatttat    1320
ttttcagcta aaattaattg caaagtgcat tgatcttata aataatttta tttatctcaa    1380
atgctatatt ggtcaaacat gtgtaattaa tagaaactta attatatttc atttatttt    1440 tcttaatctg tgtaaaaatg tcaaagtaaa atttatttag aaacgaattg agtaatattt    1500
tgtttcattt tttaaaagat atcgaatatg aaataacaca attttattgt atgatgaacc    1560
taaaaattca tcctaagaag gtgaacgcaa gaataagtca acgttttggg gaaagctaac    1620
tatggcccaa agtcatcaaa atctttcttg tatttatcaa aatccttaca aatttagtta    1680
gagttaatag accaaacaca tgattatcat catattagaa tattctaaaa aattactagc    1740
gaataattaa aatctttctt ttatttatca aaatccttat aaaaacttat ttatatatac    1800
taaaacaatt ttaattaaaa gaaaataagg gaccatggat acataaaaat atatgttatt    1860
tcttaagata gtgataatat taatatatac cagtccatat atttatcaaa ataaataata    1920
tttttcgtag tccgataatc attactataa attcataaaa ccacatgtag atgtatattt    1980
tatttatata tatatatata aaccctaacg ccttaccact cgataaccat caaaactttt    2040
cttctcgttt cgctaactca aggcttcgaa aagtaaaaaa aacaatgaag aatgtcacac    2100
ttgttcttgc tatgatcctc ttcttaagct gtgtcacatc caaagttaca gcaacagaac    2160
tagagtcatc aactaaccaa gagctcttcc tatcgcggca cttacctcgc tttcacccca    2220
agcaacattg gccgttccgt ggctccggaa aagccttccc tgcaggccac ttccgactaa    2280
ctccgttcca tctgccacag gaagtcacca gatgcttgaa cgacaagaag gaggtaggta    2340
catgttttaa tgatatcgct gagactttct tcaccaggaa agccgctatt ggatcggaat    2400
gttgcgccgc gatcaagaag atgaacaaag attgtgagaa gaccgtcttt ggatctttcc    2460
atgacccctt cttgaccggc tatgtcaagc tacattgctc caccgttgtt ggatctactt    2520
cacctcctcc ttcacaggct cctttacatg ctccttcttc acaggctcct tcacatgctc    2580
cttcacatgc tccttcacag gctcctttaa atgctccttt aaatgctcct ttacatgctc    2640
ctttacatgc tccttcacag gcccccttcac aggcccctcc ttcacatgctc    2700 ctttactgcc cccttcgcag gctccttcac cggctcagtg atttagctat ttgatagaat    2760
tattcaagta ttgatgtcct agggagtttt agttttttcc ttgttttaaa attttgtgtt    2820
tattttgaga aaaccgtctt tggatttaa ctt                                  2853
```